United States Patent
Kim et al.

(10) Patent No.: US 9,227,910 B2
(45) Date of Patent: *Jan. 5, 2016

(54) GEM-DINITRO ESTER ENERGETIC MATERIAL USING ESTERIFICATION AND PREPARATION METHOD THEREOF

(71) Applicant: AGENCY FOR DEFENSE DEVELOPMENT, Daejeon (KR)

(72) Inventors: Seung-Hee Kim, Daejeon (KR); Jin-Seuk Kim, Daejeon (KR)

(73) Assignee: AGENCY FOR DEFENCE DEVELOPMENT, Daejeon (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/289,707

(22) Filed: May 29, 2014

(65) Prior Publication Data

US 2015/0119599 A1    Apr. 30, 2015

(30) Foreign Application Priority Data

Oct. 30, 2013 (KR) .......................... 10-2013-0130059

(51) Int. Cl.
| | |
|---|---|
| *C07C 67/02* | (2006.01) |
| *C07C 205/40* | (2006.01) |
| *C06B 25/00* | (2006.01) |
| *C06B 45/10* | (2006.01) |

(52) U.S. Cl.
CPC ............... *C07C 205/40* (2013.01); *C06B 25/00* (2013.01); *C06B 45/105* (2013.01)

(58) Field of Classification Search
CPC .... A01B 12/006; C06B 25/00; C06B 45/105; C07C 69/606; C07C 205/01; C07C 205/40
See application file for complete search history.

(56) References Cited

U.S. PATENT DOCUMENTS

| | | | | |
|---|---|---|---|---|
| 2,978,494 | A * | 4/1961 | Frankel ........................ | 560/156 |
| 8,816,124 | B2 * | 8/2014 | Kwon et al. .................. | 560/222 |

OTHER PUBLICATIONS

Kissinger et al. (gem-Dinitro Esters. III. Esters of 2,2-Dinitropropanol, Journal of Organic Chemistry, 26, 5203-5, 1961).*
H. E. Ungnade et al., "Esters and Ethers of 2-Substituted 2, 2-Dinitro-I-alkanols," J. Org. Chem., vol. 31, pp. 369-371, Feb. 1966.

* cited by examiner

*Primary Examiner* — Yevegeny Valenrod
*Assistant Examiner* — Blaine G Doletski
(74) *Attorney, Agent, or Firm* — LRK Patent Law Firm

(57) ABSTRACT

This invention relates to a gem-dinitro ester energetic material represented by Chemical Formula 1 below, which is synthesized using esterification, and to a preparation method thereof:

[Chemical Formula 1]

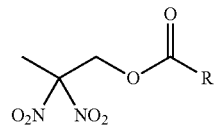

wherein R is a C5~C15 substituted or unsubstituted linear or branched alkyl group.

4 Claims, No Drawings

GEM-DINITRO ESTER ENERGETIC MATERIAL USING ESTERIFICATION AND PREPARATION METHOD THEREOF

CROSS REFERENCE TO RELATED APPLICATION

This application claims the benefit of Korean Patent Application No. KR 10-2013-0130059, filed Oct. 30, 2013, which is hereby incorporated by reference in its entirety into this application.

BACKGROUND OF THE INVENTION

1. Technical Field

The present invention relates to a gem-dinitro ester energetic material, which is synthesized using esterification, and to a preparation method thereof.

2. Description of the Related Art

A plastic bonded explosive (PBX) has been developed to improve both performance and insensitivity of explosives, and typically includes a molecular explosive in crystalline form, such as RDX (Research Department Explosive), which typically exhibits explosive performance, and a binder system. The binder system is used in an amount of about 2~20 wt % based on the total weight of PBX, and functions to impart dimensional stability and insensitivity to the molecular explosive in crystalline form. However, it does not contain a nitro group for exhibiting explosive performance as in the molecular explosive, thus deteriorating the total performance of the explosive.

The binder system is composed of a polymer and a plasticizer. As such, the amount of the plasticizer is as large as about three times the amount of the polymer, and thus the properties of the plasticizer are regarded as very important.

In order to maximize performance of PBX, thorough research into introduction of a nitro group to a plasticizer is ongoing, and a plasticizer having a nitro group is referred to as an energetic binder. The energetic binder has been extensively and intensively studied, but a typical example of the plasticizer, which is actually applied to explosives, includes a formal or acetal plasticizer, such as bis(2,2-dinitropropyl)formal (represented by Chemical Formula A below) or bis(2,2-dinitropropyl)acetal (represented by Chemical Formula B below).

[Chemical Formula A]

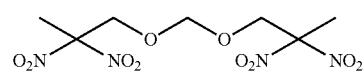

[Chemical Formula B]

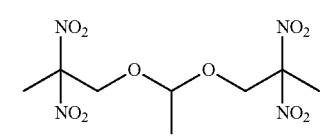

Preparation of PBX requires a mixing process. The mixing process is typically performed at 60° C. to decrease the viscosity of a polymer. The molecular explosive such as RDX used for PBX is shape-controlled in a polygonal form through recrystallization to maintain insensitivity to external impact. However, when the mixture comprising the shape-controlled molecular explosive and the energetic plasticizer mixed at 60° C. is cooled to room temperature, the shape-controlled molecular explosive is dissolved in the plasticizer and then produced again in the form of crystals. In this procedure, the molecular explosive is changed to an undesired crystal shape, such as a needle shape, etc., instead of a polygonal shape. Like this, in the case where the molecular explosive having a changed shape is contained in PBX, sensitivity of PBX increases.

The sensitivity of PBX by the plasticizer as above is based on the chemical structure of the plasticizer. Specifically, a structural difference between DOA and the energetic plasticizer depends on whether a nitro group which is an energy group is contained. When a nitro group is introduced to the plasticizer, a solid filler such as a molecular explosive is dissolved in the mixing process at 60° C. due to strong polarity of the nitro group. When the temperature is lowered, the molecular explosive is deposited again as a solid. In the deposition procedure, because the shape of the molecular explosive is changed to a sensitive shape, the molecular explosive having a changed shape makes PBX sensitive.

SUMMARY OF THE INVENTION

Accordingly, the present invention has been made keeping in mind the problems encountered in the related art, and the present inventors have ascertained the fact that the sensitivity of PBX is caused by excessive addition of a nitro group to an energetic plasticizer to increase energy density. Specifically, when the nitro group is excessively added, energy density is favorable but the viscosity of the plasticizer may rise due to the excessive nitro group, thus increasing polarity to thereby dissolve the molecular explosive, ultimately modifying the shape of the molecular explosive.

Therefore, an object of the present invention is to provide a gem-dinitro ester energetic material which is a plasticizer having a chemical structure able to minimize side-effects of dissolving the molecular explosive while increasing the energy density of PBX, and an esterification preparation method thereof.

The present invention provides a gem-dinitro ester energetic material represented by Chemical Formula 1 below:

[Chemical Formula 1]

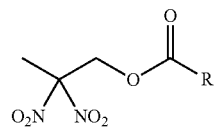

wherein R is a C5~C15 substituted or unsubstituted linear or branched alkyl group.

In addition, the present invention provides a method of preparing a gem-dinitro ester energetic material represented by Chemical Formula 1 below, including esterifying a compound represented by Chemical Formula 2 below with a compound represented by Chemical Formula 3 below:

[Chemical Formula 1]

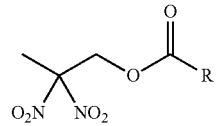

-continued

[Chemical Formula 2]

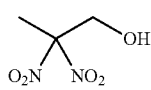

[Chemical Formula 3]

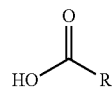

in Chemical Formulas 1 to 3, R is C5~C15 substituted or unsubstituted linear or branched alkyl group.

DESCRIPTION OF THE SPECIFIC EMBODIMENTS

The present invention addresses a gem-dinitro ester energetic material represented by Chemical Formula 1 below:

[Chemical Formula 1]

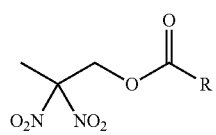

wherein R is a C5~C15 substituted or unsubstituted linear or branched alkyl group.

The C5~C15 substituted or unsubstituted linear or branched alkyl group may be, for example, a substituted or unsubstituted linear or branched hexyl group, a 2-ethylhexyl group, an octyl group, a 2-butyloctyl group or a 2-hexyldecyl group.

According to the present invention, the gem-dinitro ester energetic material may be efficiently used as a plasticizer for preparation of PBX.

According to the present invention, the gem-dinitro ester energetic material is configured such that the gem-dinitro group is introduced as an energy group, and a non-polar compound, that is, a linear or branched alkyl group is introduced to the position opposite thereto, thereby lowering the polarity of the energetic plasticizer to thus prevent shape deformation of the molecular explosive in the course of preparation of PBX, consequently decreasing impact sensitivity of PBX.

In addition, the present invention addresses a method of preparing a gem-dinitro ester energetic material represented by Chemical Formula 1 below, including esterifying a compound represented by Chemical Formula 2 below with a compound represented by Chemical Formula 3 below:

[Chemical Formula 1]

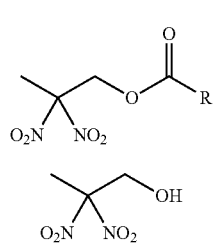

[Chemical Formula 2]

[Chemical Formula 3]

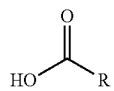

in Chemical Formulas 1 to 3, R is a C5~C15 substituted or unsubstituted linear or branched alkyl group.

The C5~C15 substituted or unsubstituted linear or branched alkyl group may be, for example, a substituted or unsubstituted linear or branched hexyl group, a 2-ethylhexyl group, an octyl group, a 2-butyloctyl group or a 2-hexyldecyl group.

[Scheme 1]

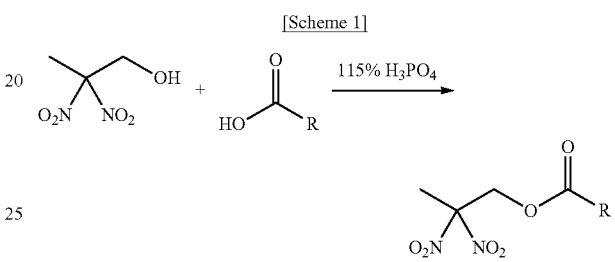

As shown in Scheme 1, the compound represented by Chemical Formula 2 and the compound represented by Chemical Formula 3 may be reacted in the presence of a catalyst, and the catalyst may be polyphosphoric acid.

Also, the reaction of the compound represented by Chemical Formula 2 and the compound represented by Chemical Formula 3 may be carried out using dichloromethane or dichloroethane as a halogen solvent.

The preparation method according to the present invention is advantageous because the gem-dinitro ester energetic material may be obtained at high yield through one-step synthesis by esterification using 2,2-dinitropropanol and a carboxylic acid compound which are commercially easily available.

Below, the present invention is described in detail through the following examples, which are merely illustrative but are not construed as limiting the present invention and may be variously varied and modified. The scope of the present invention will depend on the spirit of claims as will be described later.

EXAMPLE 1

Synthesis of 2,2-Dinitropropyl Hexanoate

[Scheme 2]

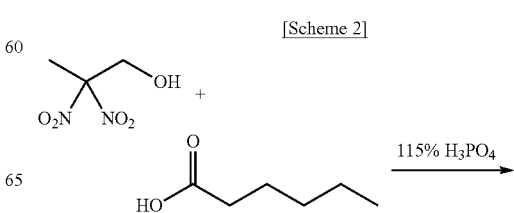

-continued

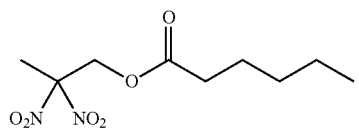

Dinitropropanol (25.5 g, 0.17 mol), hexanoic acid (21.7 g, 0.19 mol), and 50 g of polyphosphoric acid were added to 50 mL of dichloroethane, and the resulting mixture was slowly stirred using a stirrer. The solution thus obtained was slowly heated to 70° C. and then reacted for 15 hr (overnight). After the reaction, the temperature of the reactor was lowered to room temperature, and the stirrer was powered off. When the temperature of the reactor was room temperature, the dichloroethane layer was decanted, followed by extraction with a 1 N sodium hydroxide aqueous solution and then distillation under reduced pressure, affording 2,2-dinitropropyl hexanoate (39.2 g, yield: 93%).

NMR and thermoanalytical results: $^1$H NMR (CDCl$_3$) δ 4.88 (s, 2H), 2.32 (t, 2H), 2.08 (s, 3H), 1.58 (m, 2H), 1.28 (m, 4H), 0.87 (t, 3H); Tg (glass transition temperature): −101.99° C., Td (decomposition temperature): 268.00° C.

EXAMPLE 2

Synthesis of 2,2-Dinitropropyl 2-Ethylhexanoate

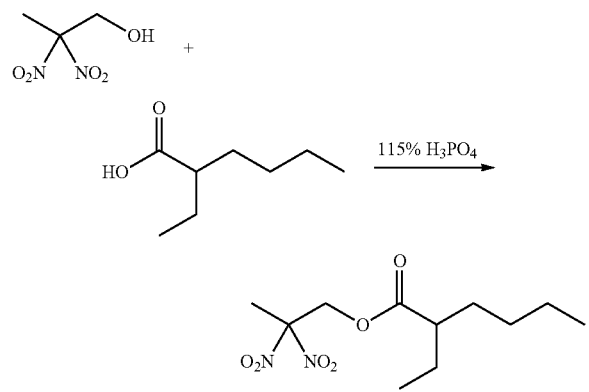

Dinitropropanol (25.5 g, 0.17 mol), 2-ethylhexanoic acid (27.4 g, 0.19 mol) and 50 g of polyphosphoric acid were added to 50 mL of dichloroethane and the resulting mixture was slowly stirred using a stirrer. The solution thus obtained was slowly heated to 70° C. and then reacted for 15 hr (overnight). After the reaction, the temperature of the reactor was lowered to room temperature, and the stirrer was powered off. When the temperature of the reactor was room temperature, the dichloroethane layer was decanted, followed by extraction with a 1 N sodium hydroxide aqueous solution and then distillation under reduced pressure, affording 2,2-dinitropropyl 2-ethylhexanoate (41.0 g, yield: 87%).

NMR and thermoanalytical results: $^1$H NMR (CDCl$_3$) δ 4.90 (s, 2H), 2.30 (m, 1H), 2.19 (s, 3H), 1.55 (m, 4H), 1.23 (m, 4H), 0.89 (m, 6H); Tg (glass transition temperature): −96.96° C., Td (decomposition temperature): 245.67° C.

EXAMPLE 3

Synthesis of 2,2-Dinitropropyl Octanoate

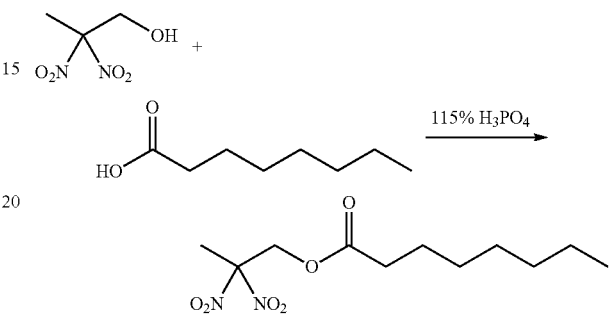

Dinitropropanol (25.5 g, 0.17 mol), octanoic acid (27.4 g, 0.19 mol) and 50 g of polyphosphoric acid were added to 50 mL of dichloroethane and the resulting mixture was slowly stirred using a stirrer. The solution thus obtained was slowly heated to 70° C. and then reacted for 15 hr (overnight). After the reaction, the temperature of the reactor was lowered to room temperature, and the stirrer was powered off. When the temperature of the reactor was room temperature, the dichloroethane layer was decanted, followed by extraction with a 1 N sodium hydroxide aqueous solution and then distillation under reduced pressure, affording 2,2-dinitropropyl octanoate (42.3 g, yield: 90%).

NMR and thermoanalytical results: $^1$H NMR (CDCl$_3$) δ 4.88 (s, 2H), 2.35 (t, 2H), 2.17 (s, 3H), 2.13 (s, 3H), 1.58 (m, 2H), 1.25 (m, 8H), 0.86 (t, 3H); Tg (glass transition temperature): −99.15° C., Td (decomposition temperature): 260.83° C.

EXAMPLE 4

Synthesis of 2,2-Dinitropropyl-2-Butyloctanoate

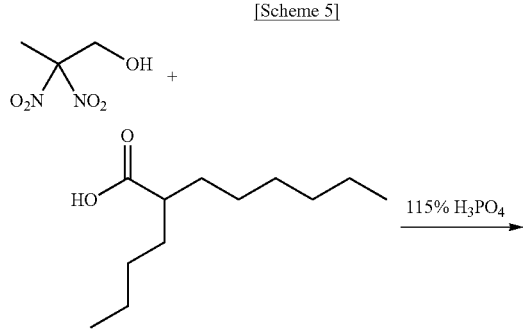

-continued

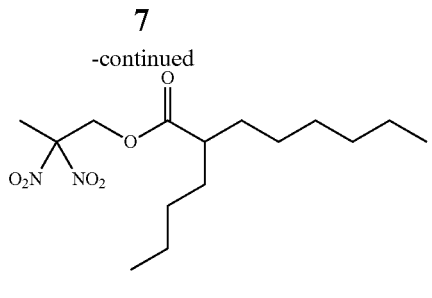

Dinitropropanol (25.5 g, 0.17 mol), 2-butyloctanoic acid (38.1 g, 0.19 mol) and 50 g of polyphosphoric acid were added to 50 mL of dichloroethane and the resulting mixture was slowly stirred using a stirrer. The solution thus obtained was slowly heated to 70° C. and then reacted for 15 hr (overnight). After the reaction, the temperature of the reactor was lowered to room temperature, and the stirrer was powered off. When the temperature of the reactor was room temperature, the dichloroethane layer was decanted, followed by extraction with a 1 N sodium hydroxide aqueous solution and then distillation under reduced pressure, affording 2,2-dinitropropyl-2-butyloctanoate (41.8 g, yield: 74%).

NMR and thermoanalytical results: $^1$H NMR (CDCl$_3$) δ 4.90 (s, 2H), 2.37 (m, 1H), 2.19 (s, 3H), 1.53 (m, 4H), 1.28 (m, 12H), 0.89 (t, 6H); Tg (glass transition temperature): −93.72° C., Td (decomposition temperature): 260.83° C.

EXAMPLE 5

Synthesis of 2,2-Dinitropropyl-2-Hexyldecanoate

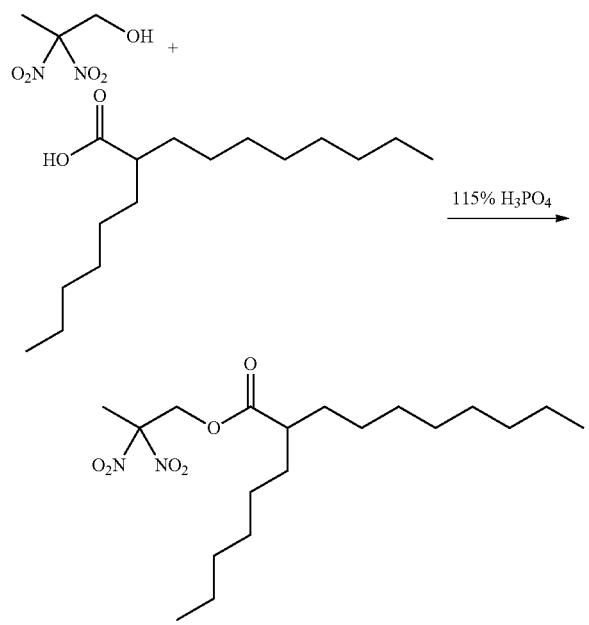

[Scheme 6]

Dinitropropanol (25.5 g, 0.17 mol), 2-hexyldecanoic acid (48.7 g, 0.19 mol) and 50 g of polyphosphoric acid were added to 50 mL of dichloroethane and the resulting mixture was slowly stirred using a stirrer. The solution thus obtained was slowly heated to 70° C. and then reacted for 15 hr (overnight). After the reaction, the temperature of the reactor was lowered to room temperature, and the stirrer was powered off. When the temperature of the reactor was room temperature, the dichloroethane layer was decanted, followed by extraction with a 1 N sodium hydroxide aqueous solution and then distillation under reduced pressure, affording 2,2-dinitropropyl-2-hexyldecanoate (39.6 g, yield: 60%).

NMR and thermoanalytical results: $^1$H NMR (CDCl$_3$) δ 4.91 (s, 2H), 2.40 (m, 1H), 2.20 (s, 3H), 1.57 (m, 4H), 1.31 (m, 22H), 0.89 (t, 6H); Tg (glass transition temperature): −92.57° C., Td (decomposition temperature): 253.33° C.

TEST EXAMPLE

Test of Impact Sensitivity of 2,2-Dinitropropyl-2-Hexyldecanoate of Example 5

The results of test of impact sensitivity of 2,2-dinitropropyl-2-hexyldecanoate (Example 5) having the greatest performance are given in Table 1 below.

TABLE 1

|  | Gem-dinitro ester (Compound of Ex. 5) | F/F |
| --- | --- | --- |
| Impact sensitivity (J) | >81.05 | 16.29 |

Note:
F/F is an abbreviation for a mixture comprising bis(2,2-dinitropropyl)formal and bis(2,2-dinitrobutyl)formal, and indicates an energetic plasticizer.

As described hereinbefore, the present invention provides a gem-dinitro ester energetic material and a preparation method thereof. According to the present invention, the gem-dinitro ester energetic material is a novel compound which is easily synthesized using a new preparation method that is different from conventional methods.

According to the present invention, the gem-dinitro ester energetic material is used as a plasticizer, thus increasing energy density of PBX and minimizing side-effects of dissolving the molecular explosive.

Therefore, the gem-dinitro ester energetic material according to the present invention can impart improvements in both explosive performance and impact insensitivity to PBX.

Also, the preparation method according to the present invention enables the gem-dinitro ester energetic material to be prepared at high yield through one-step synthesis by esterification using 2,2-dinitropropanol and a carboxylic acid compound which are commercially easily available.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A gem-dinitro ester energetic material represented by Chemical Formula 4, 5, 6, 7 or 8 below:

[Chemical Formula 4]

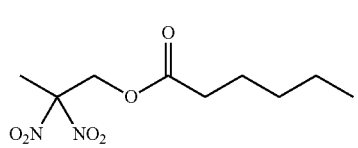

[Chemical Formula 5]

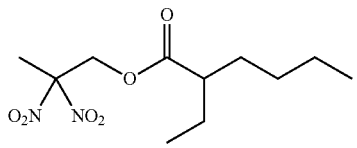

[Chemical Formula 6]

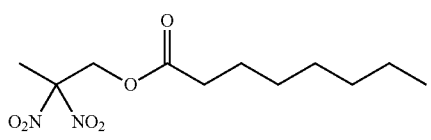

[Chemical Formula 7]

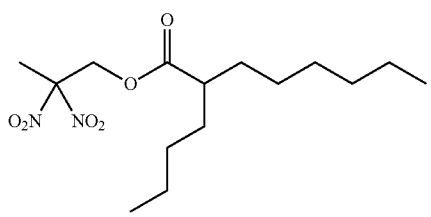

[Chemical Formula 8]

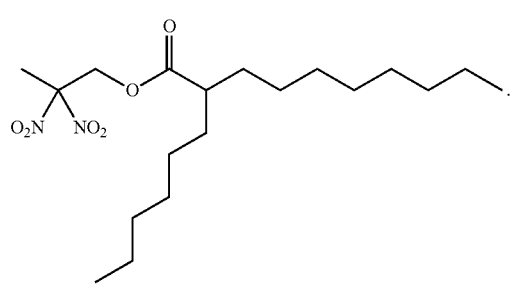

2. A method of preparing a gem-dinitro ester energetic material represented by Chemical Formula 4, 5, 6, 7 or 8 below, comprising esterifying a compound represented by Chemical Formula 2 below with a compound represented by Chemical Formula 9, 10, 11, 12 or 13 below:

[Chemical Formula 4]

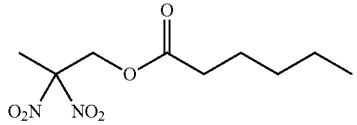

[Chemical Formula 5]

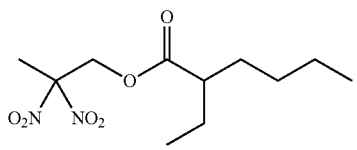

[Chemical Formula 6]

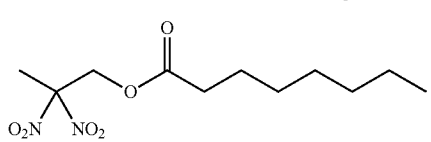

[Chemical Formula 7]

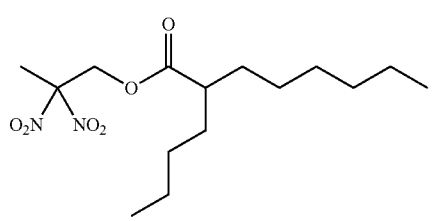

[Chemical Formula 8]

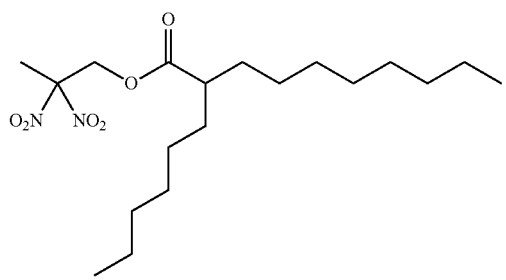

[Chemical Formula 2]

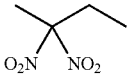

[Chemical Formula 9]

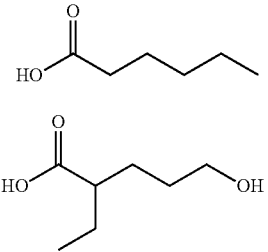

[Chemical Formula 10]

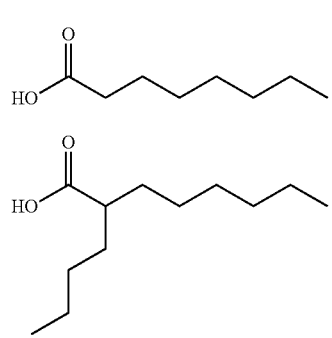

[Chemical Formula 11]

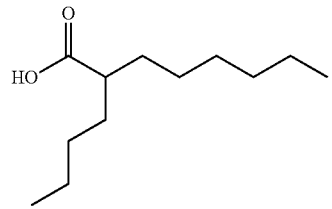

[Chemical Formula 12]

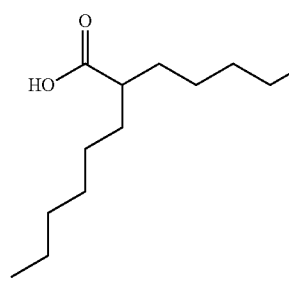

[Chemical Formula 13]

3. The method of claim 2, wherein esterifying the compound represented by Chemical Formula 2 with the compound represented by Chemical Formula 9, 10, 11, 12 or 13 is performed in the presence of polyphosphoric acid.

4. The method of claim 2, wherein esterifying the compound represented by Chemical Formula 2 with the compound represented by Chemical Formula 9, 10, 11, 12 or 13 is performed using dichloromethane or dichloroethane as a halogen solvent.

* * * * *